(12) United States Patent
Lee

(10) Patent No.: US 8,512,284 B2
(45) Date of Patent: Aug. 20, 2013

(54) MEDICAL FLUID DISPENSER

(75) Inventor: Young Gyu Lee, Seoul (KR)

(73) Assignee: Woo Young Medical Co., Ltd., Jincheon-gun, Chungcheongbuk-do (KR)

( * ) Notice: Subject to any disclaimer, the term of this patent is extended or adjusted under 35 U.S.C. 154(b) by 14 days.

(21) Appl. No.: 13/146,302

(22) PCT Filed: Jan. 28, 2010

(86) PCT No.: PCT/KR2010/000498
§ 371 (c)(1),
(2), (4) Date: Aug. 9, 2011

(87) PCT Pub. No.: WO2010/087616
PCT Pub. Date: Aug. 5, 2010

(65) Prior Publication Data
US 2011/0282283 A1    Nov. 17, 2011

(30) Foreign Application Priority Data

Jan. 28, 2009  (KR) .......................... 10-2009-0006620
Jan. 27, 2010  (KR) .......................... 10-2010-0007319

(51) Int. Cl.
*A61M 37/00*    (2006.01)

(52) U.S. Cl.
USPC ............................ 604/131; 604/132; 604/133

(58) Field of Classification Search
USPC ............... 604/131–133, 36–38, 65, 113, 136, 604/138, 151, 156
See application file for complete search history.

(56) References Cited

U.S. PATENT DOCUMENTS

| 5,219,334 A * | 6/1993 | Tsukada ..................... 604/132 |
| 6,024,724 A | 2/2000 | Lee |
| 7,264,610 B2 * | 9/2007 | Lee ............................. 604/131 |
| 2005/0075607 A1 | 4/2005 | Lee |
| 2005/0234406 A1 * | 10/2005 | Hiejima et al. ............... 604/246 |

FOREIGN PATENT DOCUMENTS

| KR | 100262930 B1 | 8/2000 |
| KR | 100514151 B1 | 9/2005 |
| KR | 100516446 B1 | 9/2005 |
| KR | 100530848 B1 | 11/2005 |
| KR | 100710898 B1 | 4/2007 |
| KR | 100919651 B1 | 9/2009 |
| KR | 101065359 B1 | 9/2011 |

* cited by examiner

*Primary Examiner* — Laura Bouchelle
(74) *Attorney, Agent, or Firm* — The Webb Law Firm

(57) ABSTRACT

The present invention provides a medical fluid dispenser. Medical fluid to be additionally administered to an administration target such as a patient is supplied into a balloon, when a button is operated. As medical fluid is supplied into the balloon, the balloon inflates to store the medical fluid therein. The inflated balloon contracts using its own restoring force to discharge the medical fluid that has been stored therein. Thereby, an additional administration of medical fluid can be continued for a predetermined time period without the need for repeatedly operating the button.

10 Claims, 14 Drawing Sheets

MEDICAL FLUID DISPENSER

TECHNICAL FIELD

The present invention relates generally to a medical fluid dispenser which is used to administer medical fluid, such as an anodyne, an antibiotic, etc. to an administration target (for example, a patient).

BACKGROUND ART

Generally, special antibiotics for cancer treatments are administered to cancer patients. In the case of patients who require pain management, anodynes are administered to them to reduce pain. Unlike general medicines, administering such special antibiotics or anodynes may lead to a coma or shock death of a patient through overdosing on medical fluid. On the other hand, if the administration amount of such medical fluid is small, it is difficult to achieve the intended purpose of the medical fluid. Therefore, it is very important to appropriately control the administration amount of medical fluid within a permissible range.

To accomplish this purpose, a medical fluid dispenser was devised. The conventional medical fluid dispenser discharges medical fluid so that medical fluid is administered to an administration target, such as a patient, at a constant administration rate. In addition, when a button is pressed, the medical fluid dispenser discharges an additional amount of medical fluid so that the administration rate of medical fluid increases. Medical fluid which is discharged from the medical fluid dispenser is injected into the administration target by an injection unit, such as an injection needle or a catheter. The additional discharge of medical fluid is realized in such a way that a bag made of elastic material, such as rubber or soft plastic, and that has stored the medical fluid therein, is compressed by the force that presses the button.

However, in the conventional medical fluid dispenser having the above-mentioned structure, when the button that has been pressed is released, the additional discharge of medical fluid is interrupted. Thus, the button must be continuously pressed until a desired amount of medical fluid is completely discharged, thereby making it inconvenient to manipulate (in particular, when an injection unit such as a catheter, having a fine passage is used to inject medical fluid, the button must be pressed several times, or for a long period of time, to discharge a desired amount of medical fluid, thus making it more inconvenient to manipulate). Therefore, improvements are required to solve these problems of the conventional technique.

DISCLOSURE

Technical Problem

Accordingly, the present invention has been made keeping in mind the above problems occurring in the prior art, and an object of the present invention is to provide a medical fluid dispenser that can continuously administer an additional amount of medical fluid to an administration target, such as a patient, for a predetermined time period despite the medical fluid dispenser being manipulated only once.

Technical Solution

In order to accomplish the above object, in an aspect, the present invention provides a medical fluid dispenser, including: a medical fluid inlet line into which medical fluid is supplied from a medical fluid supply source; a medical fluid outlet line through which the medical fluid is discharged toward an administration target; a first branch line and a second branch line branching off from the medical fluid inlet line, the first branch line and the second branch line being connected to the medical fluid outlet line; a medical fluid pumping bag provided on the first branch line, the medical fluid pumping bag storing therein medical fluid flowing along the first branch line, and being compressed by external force applied thereto to send the stored medical fluid under pressure to the medical fluid outlet line; and a temporary storage and supply means for temporarily storing the medical fluid sent under pressure from the medical fluid pumping bag and continuously discharging the temporarily stored medical fluid through the medical fluid outlet line.

The temporary storage and supply means may include a temporary storage balloon provided on the medical fluid outlet line, wherein the temporary storage balloon inflates as medical fluid sent under pressure from the first branch line is drawn into the temporary storage balloon, and the temporary storage balloon discharges the medical fluid using contractile force by which the temporary storage balloon is returned to an original state thereof.

The temporary storage and supply means may further include a medical fluid outlet tube forming a portion of the medical fluid outlet line so that medical fluid is sent under pressure from the first branch line into medical fluid outlet tube, with at least one hole formed in a circumferential surface of the medical fluid outlet tube. The temporary storage balloon may be fitted over the circumferential surface of the medical fluid outlet tube in such a way that the temporary storage balloon covers the hole so that the temporary storage balloon is inflated by medical fluid flowing out from the medical fluid outlet tube through the hole to temporarily store the medical fluid therein and is returned to the original state thereof to supply the temporarily stored medical fluid into the medical fluid outlet tube through the hole.

The medical fluid outlet tube may have a partition partitioning an inner space of the medical fluid outlet tube into an inlet side space, into which medical fluid is sent under pressure from the medical fluid pumping bag, and an outlet side space from which the medical fluid is discharged, and the hole may comprise an outflow hole communicating with the inlet side space, and an inflow hole communicating with the outlet side space.

The temporary storage and supply means may comprise a backflow prevention device preventing the temporarily stored medical fluid from flowing backwards from the temporary storage balloon toward the first branch line.

The backflow prevention device may comprise a check valve installed in the medical fluid outlet tube at a position adjacent to an inlet thereof.

Alternatively, the backflow prevention device may comprise an open and close member coming into close contact with the circumferential surface of the medical fluid outlet tube to close the outflow hole, the open and close member being moved away from the outflow hole by medical fluid sent under pressure to flow out of the outflow hole, thus opening the outflow hole. The open and close member may have a tubular shape and is fitted over the medical fluid outlet tube. The open and close member may be made of elastic material so that the open and close member is elastically brought into close contact with the outflow hole and is elastically changed in shape and moved away from the outflow hole by the medical fluid sent under pressure to flow out of the outflow hole. Furthermore, a depression for receiving the open and close member may be formed in a portion of the circumferential surface of the medical fluid outlet tube over which the open and close member is fitted.

As a further alternative, the backflow prevention device may comprise a passage opening control unit opening or closing a passage of the first branch line in such a way that when no external force is applied to the medical fluid pumping bag, the medical fluid stored in the medical fluid pumping bag is interrupted from flowing into the medical fluid outlet line, and when the external force is applied to the medical fluid pumping bag, the passage of the first branch line opens to allow the medical fluid sent under pressure from the medical fluid pumping bag to flow into the medical fluid outlet line. The passage opening control unit may open the passage of the first branch line when the compression button is pressed.

Furthermore, at least a portion of the first branch line through which medical fluid sent from the medical fluid pumping bag flows may be made of a compressible soft tube. The passage opening control unit may include: a pressing member mounted to the casing so as to be movable away from or approachable the soft tube so that when the pressing member approaches the soft tube, the pressing member compresses the soft tube to close a passage of the soft tube; a torsion spring providing elastic force to the pressing member so that the soft tube is compressed by the pressing member; and an interlocking means for transmitting operating force, generated when the compression button is pressed, to the pressing member so that the pressing member is moved away from the soft tube.

The pressing member may comprise a pressing lever having a pressing part moving away from or approaching the soft tube depending on a direction in which the pressing lever rotates. The passage opening control unit may further include a stopper disposed in a radius of rotation of the pressing part, with the soft tube located between the stopper and the pressing lever, so that the stopper assists the pressing part in compressing the soft tube.

The pressing lever may rotate around an axis parallel to a direction in which the compression button is pressed. The interlocking means may include: a driven part provided on the pressing lever; and a drive part provided on the compression button at a position at which the drive part is able to come into contact with the driven part, where at least one of contact surfaces between the drive part and the driven part may have a ramp so that when the compression button is pressed, the pressing lever rotates in a direction in which the pressing part that has compressed the soft tube releases the soft tube.

In another aspect, the present invention provides a medical fluid dispenser, including: a medical fluid inlet line into which medical fluid is supplied from a medical fluid supply source; a medical fluid outlet line through which the medical fluid is discharged toward an administration target; a first branch line and a second branch line branching off from the medical fluid inlet line, the first branch line and the second branch line being connected to the medical fluid outlet line; a medical fluid pumping bag provided on the first branch line, the medical fluid pumping bag storing therein medical fluid flowing along the first branch line, and being compressed by external force applied thereto to send the stored medical fluid under pressure to the medical fluid outlet line; and a passage opening control unit opening or closing a passage of the first branch line in such a way that when no external force is applied to the medical fluid pumping bag, the medical fluid stored in the medical fluid pumping bag is interrupted from flowing into the medical fluid outlet line, and when the external force is applied to the medical fluid pumping bag, the passage of the first branch line opens to allow the medical fluid sent under pressure from the medical fluid pumping bag to flow into the medical fluid outlet line.

Advantageous Effects

In the present invention, an additional amount of medical fluid can be administered to an administration target (a patient) for a predetermined time period by manipulating a medical fluid dispenser only once, thus making it convenient to use. Furthermore, medical fluid that is additionally administered is prevented from flowing backwards, so that medical fluid can be reliably administered to the administration target.

BEST MODE

A medical fluid dispenser according to the present invention is configured such that an administration rate of medical fluid can be momentarily increased by a simple manipulation even during the administration of medical fluid to an administration target, such as a patient, (for example, when pain lasts without subsiding even while an anodyne is being administered to reduce pain).

Figure 1:
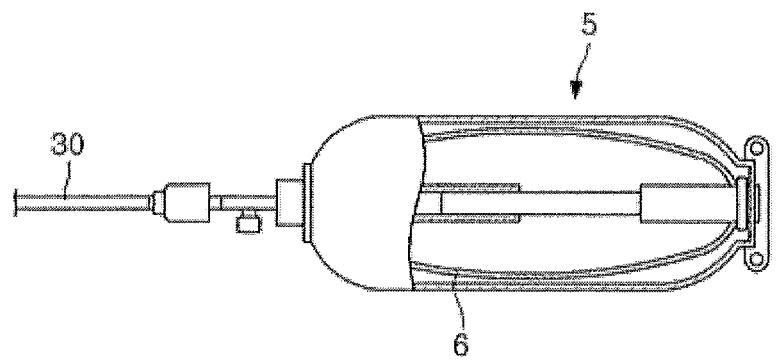
FIG. 1 is a partially sectional view showing a medical fluid supply device of a medical fluid dispenser, according to a first embodiment of the present invention.

FIG. 1 is a partially sectional view showing a medical fluid supply device of a medical fluid dispenser, according to a first embodiment of the present invention. As shown in FIG. 1, the medical fluid dispenser according to the first embodiment includes the medical fluid supply device 5. The medical fluid supply device 5 includes a medical fluid storage means 6. The medical fluid storage means 6 has an outlet through which medical fluid that has been stored therein is discharged (refer to Korean Patent Registration No. 0262930).

Figure 2:
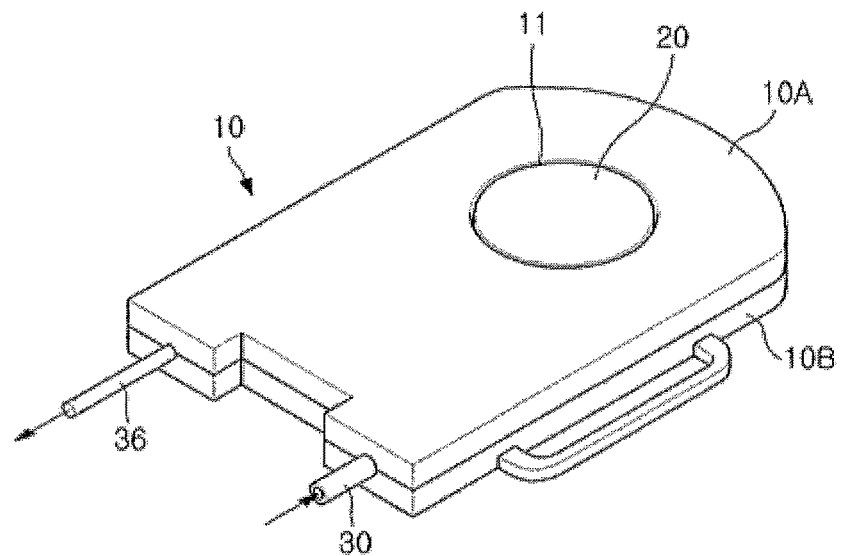
FIGS. 2 and 3 are perspective views showing a medical fluid injection device of the medical fluid dispenser according to the first embodiment of the present invention.
Figure 3:
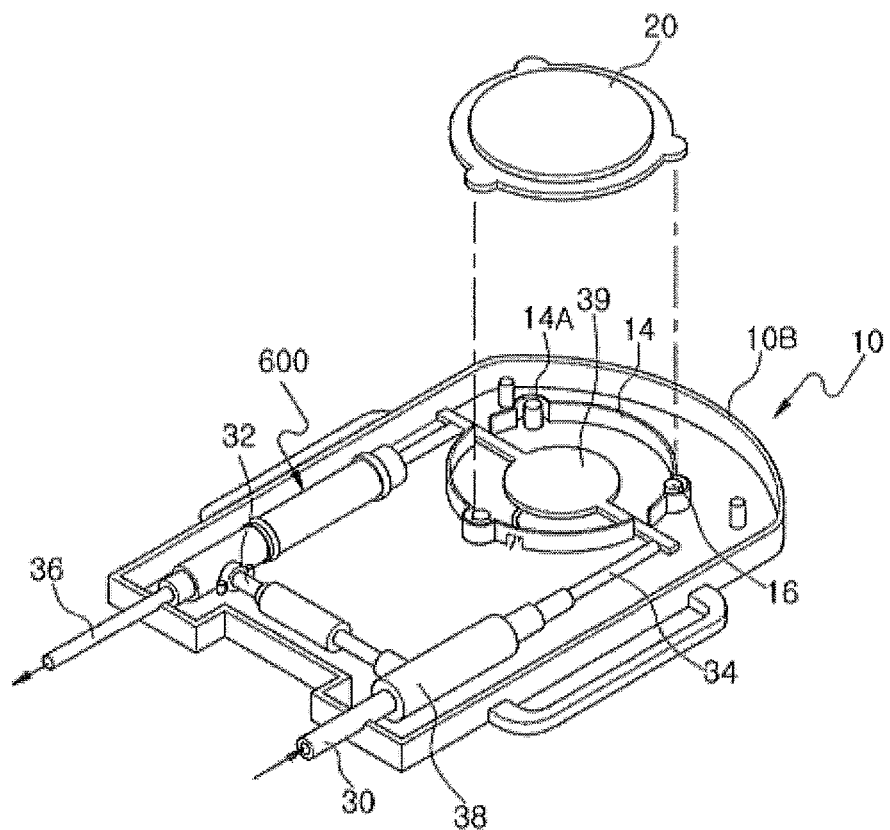

FIGS. 2 and 3 are perspective views showing a medical fluid injection device of the medical fluid dispenser according to the first embodiment of the present invention. As shown in FIGS. 2 and 3, the medical fluid dispenser according to the first embodiment further includes the medical fluid injection device 10 that injects medical fluid into the administration target from the medical fluid supply device 5. The medical fluid injection device 10 includes a medical fluid inlet line into which medical fluid is supplied from the medical fluid storage means 6, and a medical fluid outlet line through which medical fluid to be administered into the administration target is discharged out of the medical fluid injection device 10. An injection unit, such as an injection needle or catheter, is connected to an end of the medical fluid outlet line. The medical fluid injection device 10 further includes a first branch line 34 and a second branch line 32 which are bifurcated from the medical fluid inlet line and are connected to the medical fluid outlet line, and a medical fluid pumping bag 39 which is provided on the first branch line 34.

The medical fluid inlet line includes a medical fluid inlet hose 30 which is connected to the medical fluid storage means 6. The medical fluid outlet line includes a medical fluid outlet hose 36. The two branch lines 32 and 34 are connected to the medical fluid inlet hose 30 by a connector 38 which has an inner space as a medical fluid inlet chamber. Medical fluid which flows along the first branch line 34 toward the medical fluid outlet line is drawn into the medical fluid pumping bag 39. The medical fluid pumping bag 39 is made of material (preferably, elastic material) which is able to change in shape when external pressure is applied thereto.

In this embodiment, medical fluid that is supplied from the medical fluid storage means 6 flows along the medical fluid inlet hose 30 and then is drawn into the medical fluid inlet chamber (that is, into the inner space of the connector 38). Thereafter, the medical fluid is distributed from the medical fluid inlet chamber into the two branch lines 32 and 34 before being injected into the administration target through the medical fluid outlet hose 36. When pressure is applied to the medical fluid pumping bag 39, the medical fluid pumping bag 39 is compressed. Then, medical fluid that has been drawn into the medical fluid pumping bag 39 through the first branch line 34 and stored in the medical fluid pumping bag 39 is sent under pressure toward the medical fluid outlet line by the compression of the medical fluid pumping bag 39. Thereby, the administration rate of medical fluid to the administration target is momentarily increased.

The medical fluid injection device 10 further includes casings 10A and 10B. The casings 10A and 10B contain the two branch lines 32 and 34, the medical fluid pumping bag 39 and the connector 38 therein. The casings 10A and 10B comprise an upper casing 10A and a lower casing 10B that are coupled to each other. The two branch lines 32 and 34 and the medical fluid pumping bag 39 are placed on the bottom of the lower casing 10B. A compression button 20 is disposed above the medical fluid pumping bag 39 to apply pressure to the medical fluid pumping bag 39.

The compression button 20 is installed in the casings 10A and 10B such that it is able to be pressed by a user. Thus, when the user presses the compression button 20, pressure is applied to the medical fluid pumping bag 39. To realize this structure, a guide 14 is provided on the bottom of the lower casing 10B to guide vertical movement of the compression button 20. The guide 14 comprises a pair of guides 14. The compression button 20 is disposed between the pair of guides 14. The guides 14 have spring seating depressions 14A therein. Coil springs 16 are provided in the respective spring seating depressions 14A. The coil springs 16 are elastic members used to return the compression button 20 that has been pressed to its original position. The upper casing 10A has an opening 11 through which a central portion of the compression button 20 is exposed outside the casings 10A and 10B. When the user presses the portion of the compression button 20 that is exposed to the outside through the opening 11, the medical fluid pumping bag 39 is compressed by the compression force of the compression button 20 to send medical fluid under pressure. At this time, the coil springs 16 are compressed. When the user releases the compression button 20, the compression button 20 is returned to its original position by the restoring force of the coil spring 16 that has been compressed, and the medical fluid pumping bag 39 is filled with medical fluid.

The medical fluid dispenser according to the first embodiment further includes a temporary storage and supply means 600 that temporarily stores medical fluid, which is sent under pressure thereinto from the medical fluid pumping bag 39 along the first branch line 34 by pressing the compression button 20, and then continuously discharges the stored medical fluid to the medical fluid outlet line for a predetermined time period.

Figure 4:
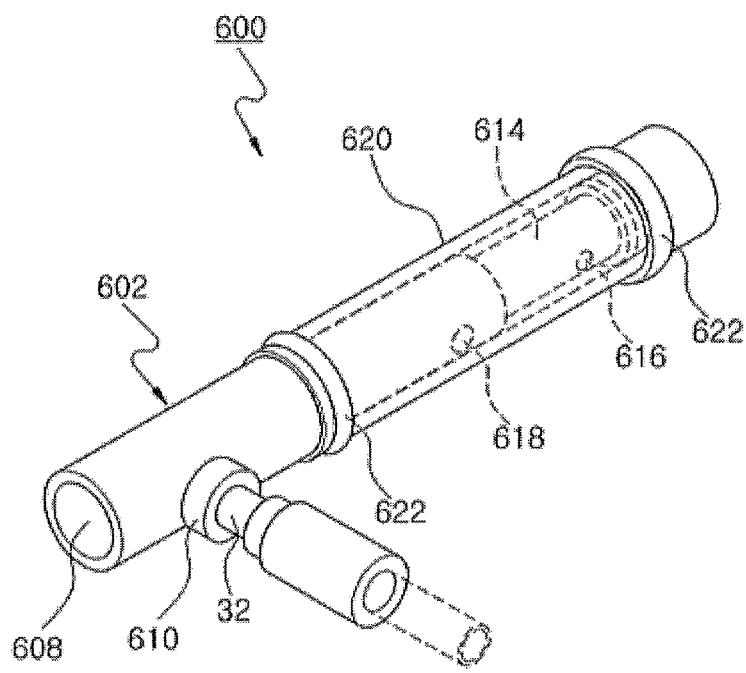
FIGS. 4 through 6 are, respectively, a perspective view, an exploded perspective view and a longitudinal sectional view showing a temporary storage and supply means shown in FIG. 3.
Figure 5:
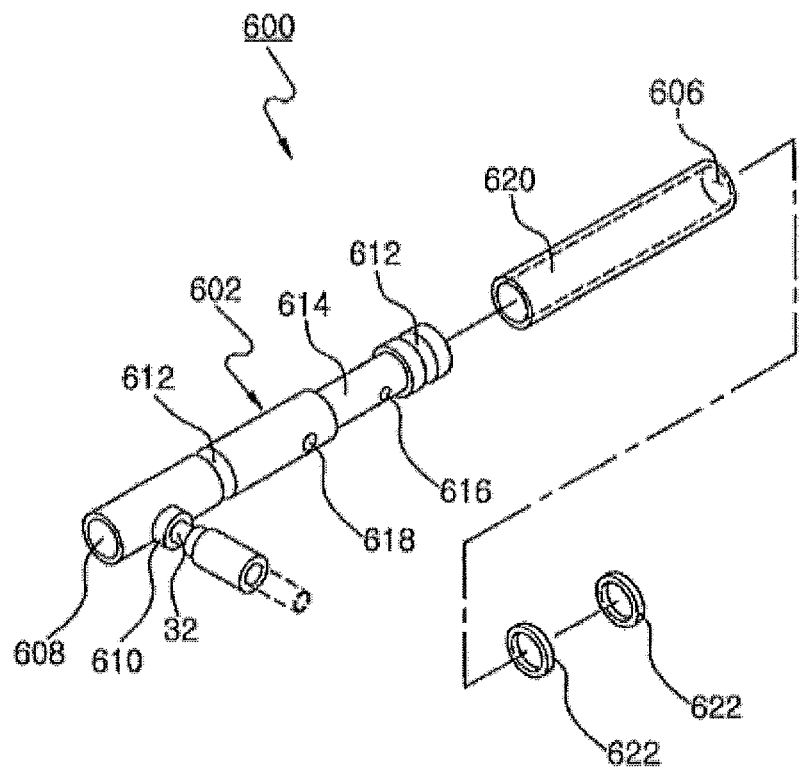
Figure 6:
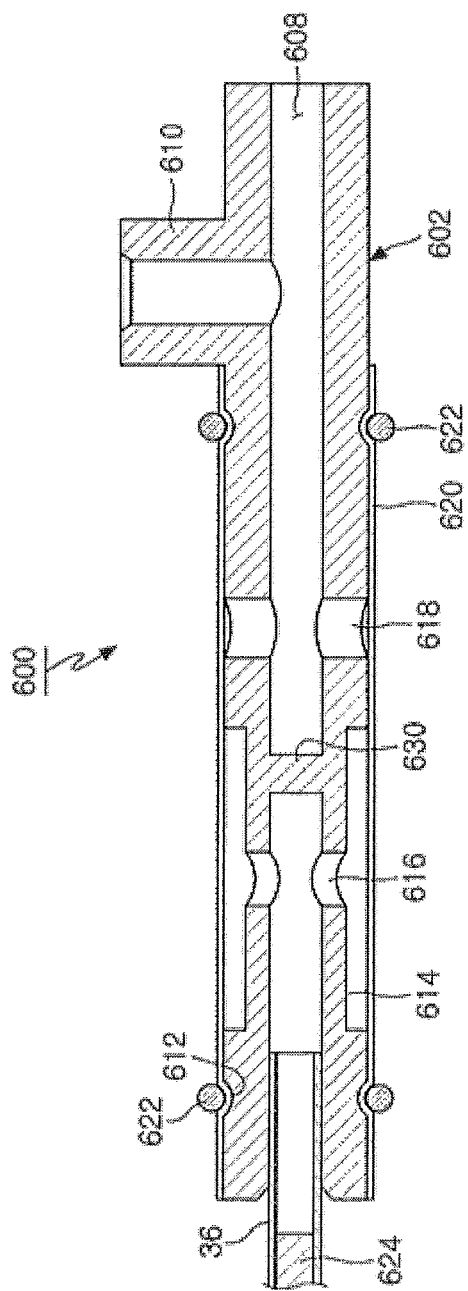

FIGS. 4 through 6 are, respectively, a perspective view, an exploded perspective view and a longitudinal sectional view showing the temporary storage and supply means 600. As shown in FIGS. 4 through 6, the temporary storage and supply means 600 is installed in the casings 10A and 10B between the first branch line 34 and the medical fluid outlet hose 36 and is configured such that medical fluid that is sent under pressure from the medical fluid pumping bag 39 along the first branch line 34 is supplied into the medical fluid outlet hose 36. Furthermore, the temporary storage and supply means 600 includes a medical fluid outlet tube 602, a temporary storage balloon 620 and a backflow prevention device.

The medical fluid outlet tube 602 along with the medical fluid outlet hose 36 constitutes the medical fluid outlet line. One end (an inlet 606) of both ends of the medical fluid outlet tube 602 is connected to the first branch line 34, and the other end (an outlet 608) of the medical fluid outlet tube 602 is connected to the medical fluid outlet hose 36. A connector 610 is integrally provided on the medical fluid outlet tube 602 at a position adjacent to the outlet 608. The second branch line 32 is connected to the integrated connector 610. At least one outflow hole 616 and at least one inflow hole 618 are formed in a circumferential surface of the medical fluid outlet tube 602. Medical fluid flows from the first branch line 34 out of the medical fluid outlet tube 602 through the outflow hole 616 in radial directions of the medical fluid outlet tube 602. The medial fluid is drawn into the medical fluid outlet tube 602 through the inflow hole 618. The outflow hole 616 and the inflow hole 618 are spaced apart from each other in a longitudinal direction of the medical fluid outlet tube 602 by a predetermined distance.

The medical fluid outlet tube 602 includes a partition 630 which partitions an inner space (that is, a passage) of medical fluid outlet tube 602 into two spaces including an inlet side space (connected to the inlet 606 into which medical fluid sent under pressure is supplied) that communicates with the outflow hole 616, and an outlet side space (connected to the outlet 608 through which the medical fluid is discharged therefrom) that communicates with the inflow hole 618. Thus, medical fluid that is supplied into the medical fluid outlet tube 602 flows out through the outflow hole 616 rather than through the inflow hole 618.

The temporary storage balloon 620 comprises a tube that is fitted over the circumferential surface of the medical fluid outlet tube 602 and covers the outflow hole 616 and the inflow hole 618. Preferably, the temporary storage balloon 620 is made of material having superior elasticity. Each of both ends of the temporary storage balloon 620 is fastened to the medical fluid outlet tube 602 by a fastening band 622. As medical fluid that has been sent under pressure into the medical fluid outlet tube 602 flows out of the outflow hole 616, the temporary storage balloon 620 inflates and temporarily stores the medical fluid therein. The medical fluid that has been temporarily stored in the temporary storage balloon 620 is drawn into the medical fluid outlet tube 602 through the inflow hole 618 by the contractile force of the temporary storage balloon 620 that is returned to its original state.

In this embodiment, although the temporary storage balloon 620 has been illustrated as being fastened to the medical fluid outlet tube 602 by the fastening bands 622, both ends of the temporary storage balloon 620 may be adhered to the medical fluid outlet tube 602.

Preferably, fastening depressions 612 are formed in portions of the circumferential outer surface of the medical fluid outlet tube 602 to which both ends of the temporary storage balloon 620 are fastened, so that the fastening bands 622 are inserted into the respective fastening depressions 612. Thereby, the fastening bands 622 can be prevented from being undesirably displaced from the correct positions.

Furthermore, a portion (see reference numeral 614) of the circumferential outer surface of the medical fluid outlet tube 602 which has the outflow hole 616 therein has a reduced outer diameter so that the reduced-diameter portion is spaced apart from the temporary storage balloon 620 that is in the original state. A portion of the circumferential outer surface of the medical fluid outlet tube 602 which has the inflow hole 618 therein has a predetermined outer diameter through which it is in close contact with the temporary storage balloon 620 that is in the original state. In this structure, the outflow hole 616 is always in an open state, but the inflow hole 618 is closed by the temporary storage balloon 620 that is in the original state. This structure provides the following advantage, considering the operation of the temporary storage and supply means 600 in which when the compression button 20 is pressed to administer an additional amount of medical fluid to the administration target, medical fluid sent under pressure from the medical fluid pumping bag 39 is continuously discharged for a predetermined time period. That is, the above-stated reduced-diameter portion structure can prevent the outer hole 616 from being closed by the temporary storage balloon 620, thus avoiding a problem in which the pressure of medical fluid sent from the first branch line 34 may not be able to overcome the elastic force of the temporary storage balloon 620 and the medical fluid may not be discharged from the medical fluid outlet tube 602.

The backflow prevention device functions to prevent medical fluid, which is temporarily stored in the temporary storage balloon 620 before flowing toward the outlet 608, from flowing backwards to the first branch line 34. The backflow prevention device includes a check valve 624 which is installed in the medical fluid outlet tube 602 at a position adjacent to the inlet 606.

Figure 7:
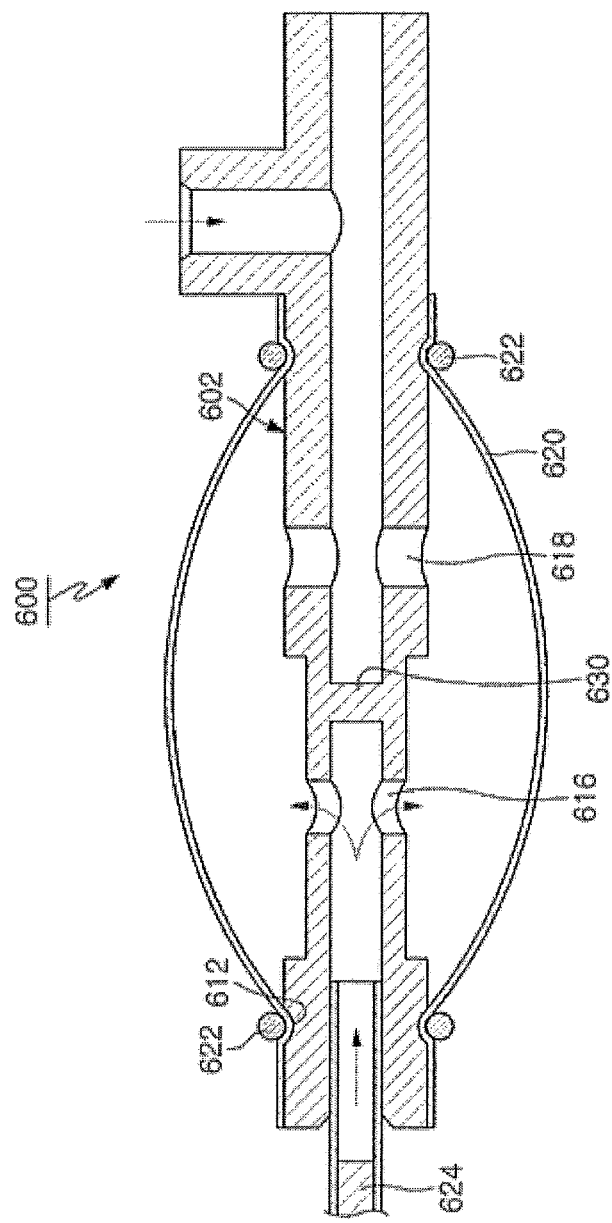
FIGS. 7 and 8 are sectional views showing the operation of the temporary storage and supply means of the medical fluid dispenser according to the first embodiment, which continuously administers an additional amount of medical fluid for a predetermined time period.
Figure 8:
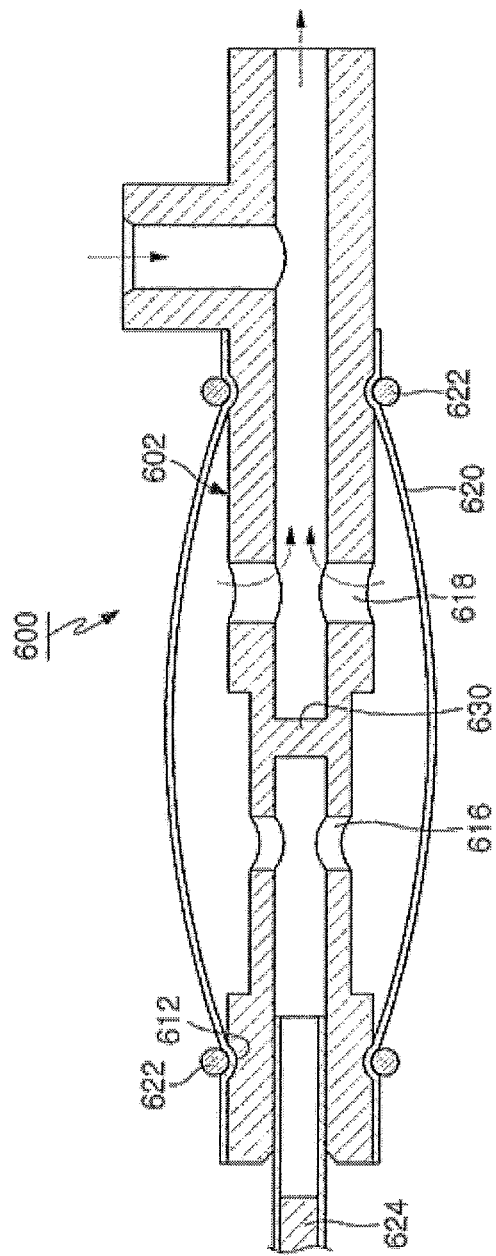

FIGS. 7 and 8 are sectional views showing the operation of the temporary storage and supply means 600 which continuously administers an additional amount of medical fluid for a predetermined time period. The operation of the first embodiment will be explained in detail with reference to these drawings.

The medical fluid injection device 10 continuously supplies medical fluid from the medical fluid supply device 5 to the administration target via the second branch line 32. During this process, when the compression button 20 is pushed, medical fluid which has been stored in the medical fluid pumping bag 39 is sent under pressure to the temporary storage and supply means 600 through the first branch line 34. In detail, as shown in FIG. 7, medical fluid sent under pressure from the medical fluid pumping bag 39 is drawn into the medical fluid outlet tube 602, flows out of the medical fluid outlet tube 602 through the outflow hole 616, and enters the temporary storage balloon 620. Then, the temporary storage balloon 620 is inflated by the medical fluid supplied thereinto.

Thereafter, as shown in FIG. 8, the temporary storage balloon 620 which has inflated is returned to its original state by its own elastic force. Then, the medical fluid which has been stored in the temporary storage balloon 620 is drawn into the medical fluid outlet tube 602 through the inflow hole 618 by the contractile force of the temporary storage balloon 620 and flows along the medical fluid outlet hose 36 before being administered to the administration target. During this process, the medical fluid which flows out of the temporary storage balloon 620 is prevented from flowing backwards by the check valve 624 which is installed in the medical fluid outlet tube 602 at a position adjacent to the inlet 606.

As stated above, in the medical fluid dispenser according to the first embodiment, when the compression button 20 is compressed to administer an additional amount of medical fluid, that has been stored in the medical fluid pumping bag 39, to the administration target, medical fluid that is sent under pressure from the medical fluid pumping bag 39 is temporarily stored in the temporary storage balloon 620 and then is continuously discharged therefrom for a predetermined time period, thus making it more convenient to use. Furthermore, the check valve 624 prevents medical fluid that flows out of the temporary storage balloon 620 from flowing backwards, so that an additional amount of medical fluid can be reliably administered to the administration target.

In the above-mentioned medical fluid administration process, if an injection unit having a fine passage is used, because a flow rate of medical fluid drawn into the temporary storage balloon 620 is greater than a flow rate of medical fluid that is typically directly supplied to the medical fluid outlet hose 36, the temporary storage balloon 620 is easily inflated compared to that of an injection unit having a thick passage. Considering the inflation efficiency of the temporary storage balloon 620, it is preferable that the injection unit be of a type having a fine passage.

Figure 9:
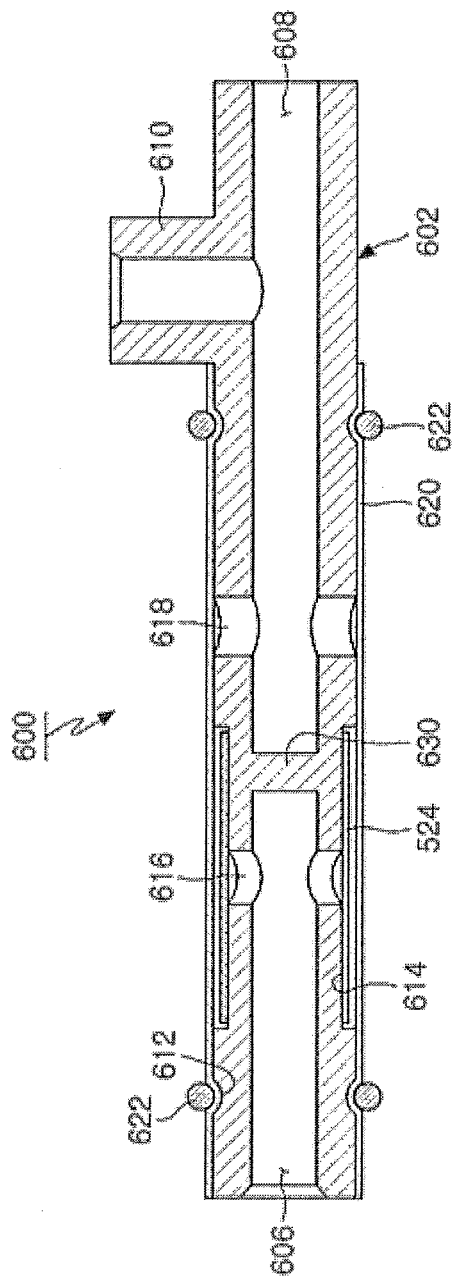
FIG. 9 is a longitudinal sectional view showing a critical portion of a medical fluid dispenser, according to a second embodiment of the present invention.

FIG. 9 is a sectional view showing a critical portion of a medical fluid dispenser, according to a second embodiment of the present invention. As shown in FIG. 9, the generation construction and operation of the medical fluid dispenser of the second embodiment, except for the construction of a backflow prevention device, remain the same as the first embodiment.

The backflow prevention device according to the second embodiment includes an open and close member 524. The open and close member 524 has a tubular shape and is made of elastic material, such as silicone, having superior elasticity. The open and close member 524 is tightly fitted over the surface of the depression 614 which is formed in the circumferential direction in the portion of the circumferential outer surface of the medical fluid outlet tube 602 that has the outflow hole 616 therein. The open and close member 524 closes the outflow hole 616 using its own elastic force. The open and close member 524 is spaced apart from the outflow hole 616 by the pressure of medical fluid that is sent under pressure from the first branch line 34 to flow out of the outflow hole 616, thus opening the outflow hole 616. The open and close member 524 may be partially adhered to the surface of the depression 614 of the medical fluid outlet tube 602, without impeding the operation of the open and close member 524 that comes into close contact with the surface of the depression 614 and is spaced apart therefrom, or medical fluid flowing into the temporary storage balloon 620.

Figure 10:
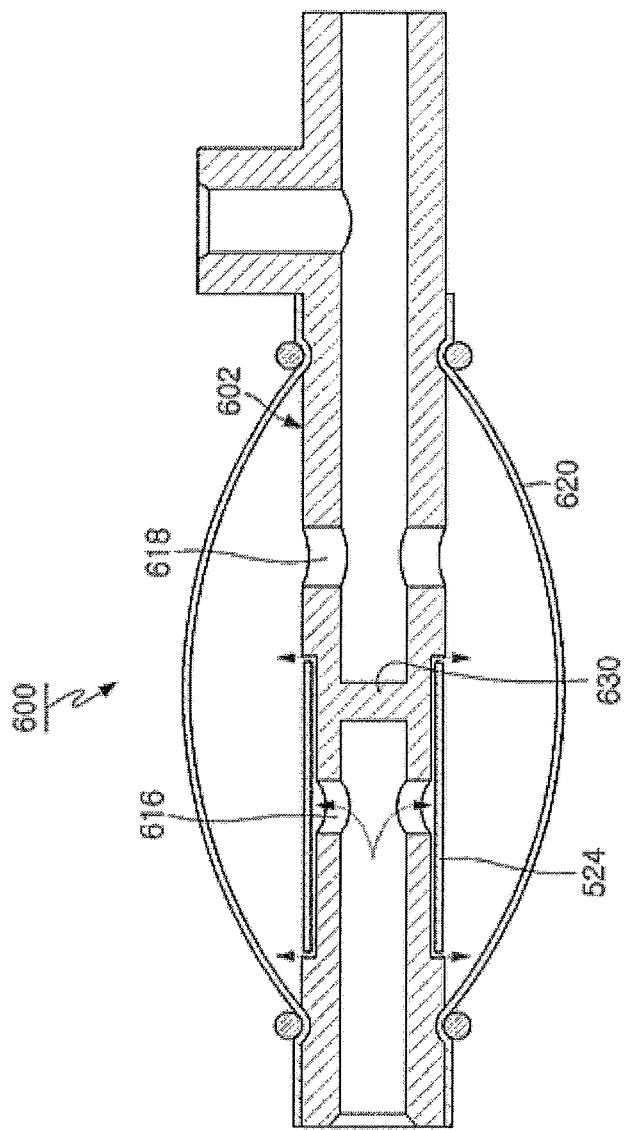
FIGS. 10 and 11 are sectional views showing the operation of a temporary storage and supply means of the medical fluid dispenser according to the second embodiment, which continuously administers an additional amount of medical fluid for a predetermined time period.
Figure 11:
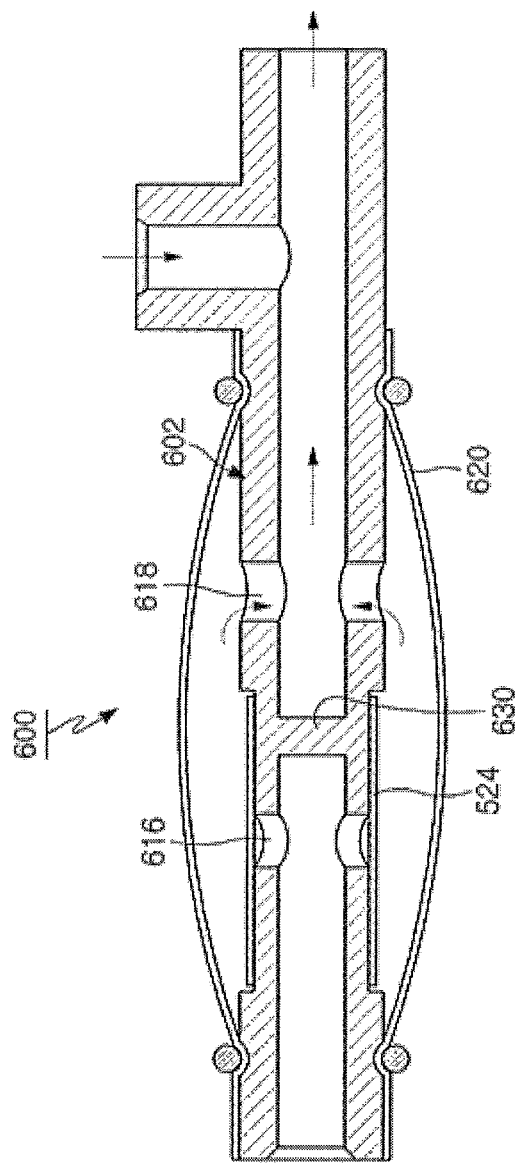

FIGS. 10 and 11 illustrate the operation of the open and close member 524. When medical fluid is sent under pressure from the medical fluid pumping bag 39, as shown in FIG. 10, the open and close member 524 that has been brought into close contact with the surface of the surface of the depression 614 by its own elastic force and closed the outflow hole 616 is pushed outwards by the pressure of the medical fluid which is sent under pressure to flow out of the outflow hole 616. Thereby, the open and close member 524 is spaced apart from the outflow hole 616, thus opening the outflow hole 616. The medical fluid that flows out of the open outflow hole 616 is supplied into the temporary storage balloon 620 through space formed between the open and close member 524 and the surface of the depression 614. The temporary storage balloon 620 is inflated by the medical fluid supplied thereinto.

Subsequently, when medical fluid is no longer supplied from the outflow hole 616 into the temporary storage balloon 620, the open and close member 524 is returned to its original state, as shown in FIG. 11. Then, the outflow hole 616 is closed, and medical fluid that has been stored in the temporary storage balloon 620 is prevented from flowing backwards into the outflow hole 616 by the open and close member 524 that closes the outflow hole 616.

Figure 12:
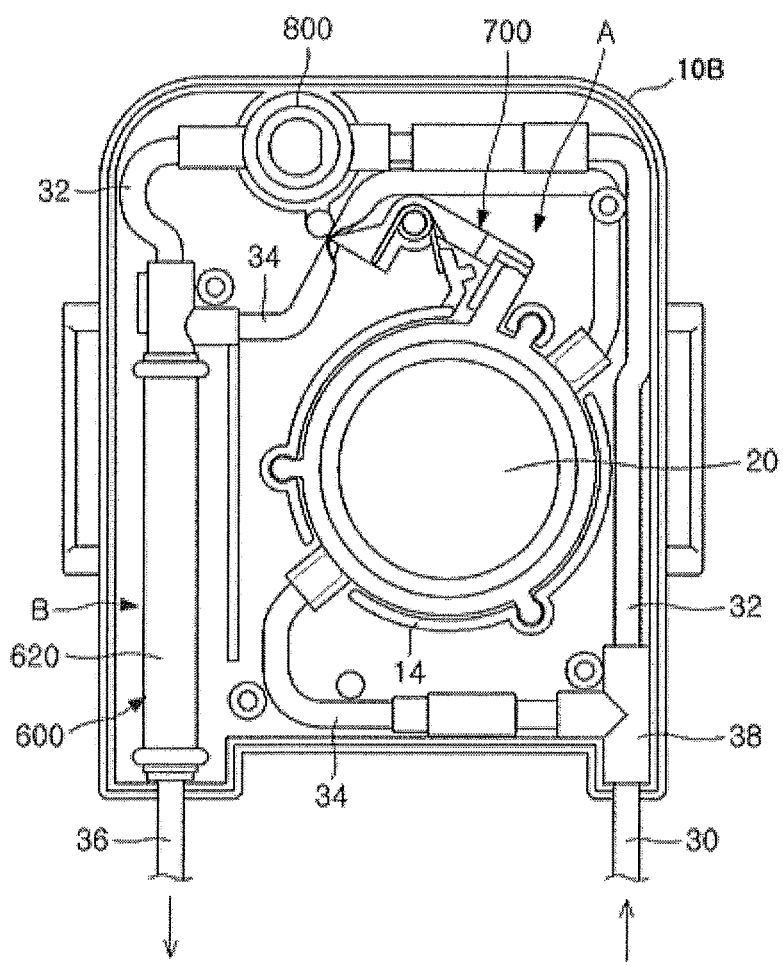
FIG. 12 is a front view showing a critical portion of a medical fluid dispenser, according to a third embodiment of the present invention.
Figure 13:
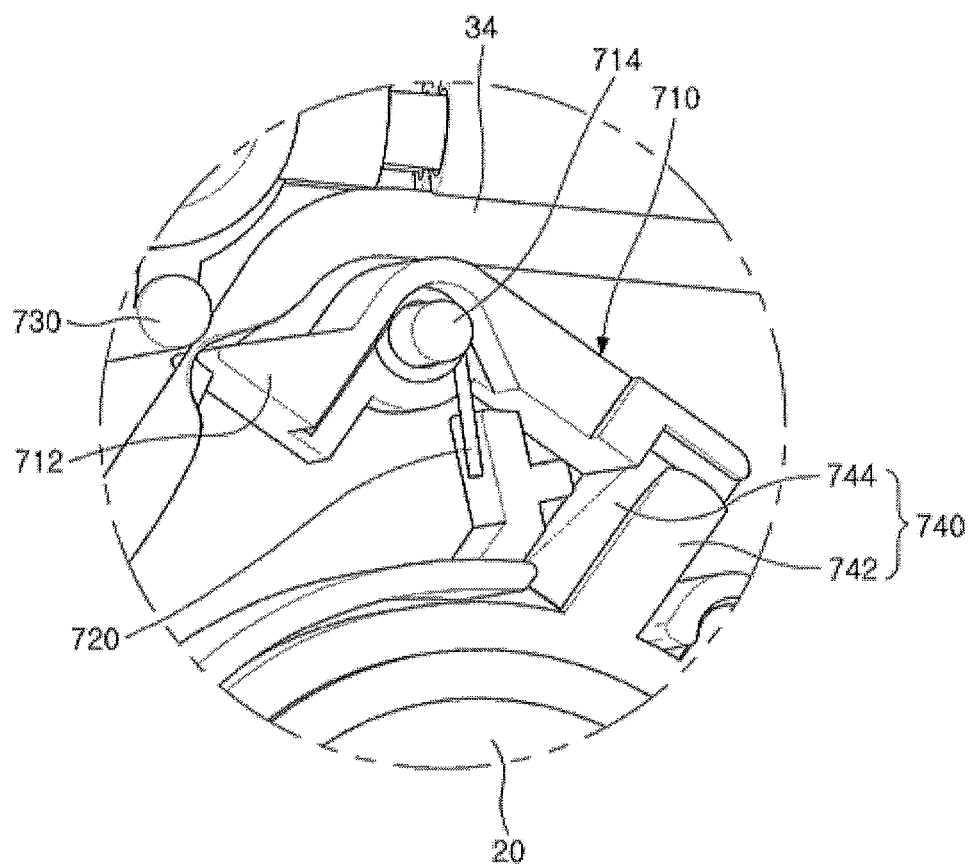
FIG. 13 is an enlarged view of portion A of FIG. 12.
Figure 14:
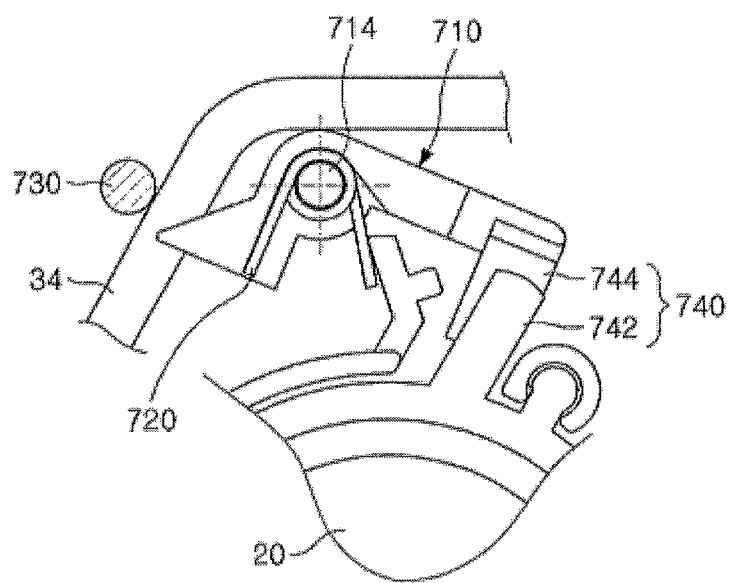
FIG. 14 is a front view showing the operation of a backflow prevention device shown in FIGS. 12 and 13.
Figure 15:
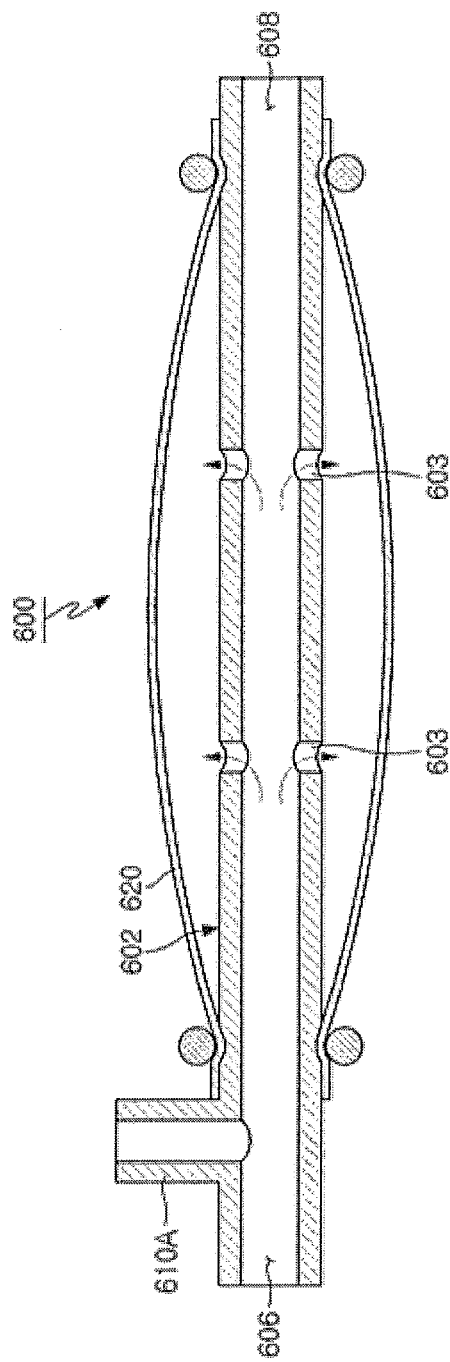
FIG. 15 is a sectional view showing the operation of portion B of FIG. 12.

FIG. 12 is a front view showing a critical portion of a medical fluid dispenser, according to a third embodiment of the present invention. FIG. 13 is an enlarged view of portion A of FIG. 12. FIG. 14 is a front view showing the operation of a backflow prevention device shown in FIGS. 12 and 13. FIG. 15 is a sectional view showing the operation of portion B of FIG. 12. As shown in FIGS. 12 through 15, the general construction and operation of the medical fluid dispenser according to the third embodiment are the same as those of the first or second embodiment, but the construction of the backflow prevention device and a temporary storage and supply means 600 and the installation structures of first and second branch lines 34 and 32 differ from those of the first or second embodiment.

The backflow prevention device according to the third embodiment includes a passage opening control unit 700 that opens or closes the passage of the first branch line 34 depending on manipulation of a compression button 20. In detail, only when the compression button 20 is being pressed, the passage opening control unit 700 opens the first branch line 34 so that medical fluid is sent under pressure from a medical fluid pumping bag 39 into the temporary storage and supply means 600. The passage opening control unit 700 includes a pressing lever 710, a torsion spring 720, a stopper 730 and an interlocking means 740.

A pressing part 712 is provided on one of both ends of the pressing lever 710. The pressing part 712 compresses a portion of the first branch line 34 through which medical fluid is sent under pressure from the medical fluid pumping bag 39, thus closing the passage of the first branch line 34. At least a corresponding portion (hereinafter, referred to as 'a compression portion') of the first branch line 34 is made of a soft tube so that it can be compressed by the compressing operation of the pressing part 712. Furthermore, the pressing lever 710 is disposed between the first branch line 34 and the compression button 20 at a position adjacent to the compression portion of the first branch line 34. In addition, the pressing lever 710 is provided on the bottom of a lower casing 10B so as to be rotatable at a predetermined angle around an axis parallel to the direction in which the compression button 20 is pressed. Thus, depending on the direction in which the pressing lever 710 rotates, the pressing part 712 moves away from the compression portion or approaches it. To realize the angle motion of the pressing lever 710, the pressing lever 710 has on a medial portion thereof a hinge shaft 714 that is oriented in the direction in which the compression button 20 is pressed.

The torsion spring 720 provides elastic force to the pressing lever 710 so that the compression portion of the first branch line 34 is maintained in a state of being compressed by the pressing part 712. In other words, the torsion spring 720 applies force to the pressing lever 710 to rotate the pressing lever 710 in the direction in which the pressing part 712 approaches the compression portion of the first branch line 34 so that the pressing part 712 compresses the compression portion of the first branch line 34 using the force transmitted from the torsion spring 720. Preferably, the torsion spring 720 is provided on the hinge shaft 714. A first end of both ends of the torsion spring 720 is supported on the pressing part 712, and a second end thereof is supported on a peripheral structure. For reference, in this embodiment, the second end of the torsion spring 720 is supported on the guide 14 which is of the peripheral structure. The guide 14 may have a support to form a structure for supporting the torsion spring 720.

The stopper 730 is disposed in a radius of rotation of the pressing part 712, and the compression portion of the first branch line 34 is located between the stopper 730 and the pressing lever 710. The stopper 730 assists the pressing part 712 in compressing the compression portion of the first branch line 34. Due to the stopper 730, the compression portion of the first branch line 34, which is made of a soft tube, can be reliably compressed by the pressing part 712 without being pushed out in the direction in which the compression force is applied thereto.

The interlocking means 740 is configured such that when the compression button 20 is pressed, the pressing force is transmitted to the pressing lever 710 so that the pressing part 712 is spaced apart from the compression portion of the first branch line 34. The interlocking means 740 includes a drive part 742 and a driven part 744. The drive part 742 is provided on the compression button 20 in a shape in which it protrudes toward the second end of the pressing lever 710. Thus, the drive part 742 is operated along with the compression button 20. The driven part 744 is provided on the second end of the pressing lever 710 at a position corresponding to the drive part 742 so that the lower surface of the drive part 742 is able to come into contact with the driven part 744. Preferably, the drive part 742 and the driven part 744 are respectively integrally provided on the compression button 20 and the pressing lever 710.

At least one of contact surfaces between the drive part 742 and the driven part 744 comprises a curved or planar ramp. In this embodiment, both the contact surfaces between the drive part 742 and the driven part 744 comprise ramps. The ramp of the drive part 742 is inclined upwards toward the driven part 744. The ramp of the driven part 744 is inclined downwards towards the drive part 742.

With regard to the interlocking means 740 having the above-mentioned structure, when the user presses the compression button 20, the ramp of the drive part 742 comes into contact with and pushes the ramp of the driven part 744, thus rotating the pressing lever 710 of the passage opening control unit 700, which has compressed the compression portion of the first branch line 34 using the elastic force of the torsion spring 720 and closed the passage of the compression portion. Thereby, the pressing part 712 is moved away from the compression portion of the first branch line 34 to release the compression portion of the first branch line 34, thus opening the passage of the first branch line 34 (refer to FIG. 14). At this time, medical fluid that is sent under pressure from the medical fluid pumping bag 39 is drawn into the temporary storage and supply means 600. When the user releases the compression button 20, the pressing lever 710 is rotated and returned to its original position by the restoring force of the torsion spring 720 so that the compression portion of the first branch line 34 is compressed again by the pressing part 712 (refer to FIG. 13).

Meanwhile, unlike the first or second embodiment, the temporary storage and supply means 600 does not requires a partition 630 in a medical fluid outlet tube 602, because the passage opening control unit 700 is provided on the first branch line 34. Furthermore, in place of the outflow hole 616 and the inflow hole 618, at least one inflow and outflow hole 603 is formed in a circumferential surface of the medical fluid outlet tube 602. Medical fluid that is sent under pressure from the medical fluid pumping bag 39 into the medical fluid outlet tube 602 can flow out of the medical fluid outlet tube 602 through the inflow and outflow hole 603 and enter into the temporary storage balloon 620, and the medical fluid that has been stored in the temporary storage balloon 620 can be drawn into the medical fluid outlet tube 602 through the inflow and outflow hole 603 again.

In the drawings, reference numeral 610A denotes a connector that performs the same function as that of the connector 610. The second branch line 32 is connected to the medical fluid outlet tube 602 at a position adjacent to the inlet 606 by the connector 610A Furthermore, in FIG. 12, reference numeral 800 denotes an administration rate control device that is provided on the second branch line 32. The administration rate control device 800 is configured in such a way that medical fluid drawn thereinto along the second branch line 32 is distributed to a plurality of distribution tubes that have different cross-sectional areas of passages, and the distributed medical fluid are switched by a multi-valve so that the flow rate of medical fluid can be controlled at various levels, thus making it possible to precisely control the rate at which medical fluid is administered to the administration target (refer to Korean Patent Application No. 2009-0008090).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A medical fluid dispenser, comprising:
a medical fluid inlet line into which medical fluid is supplied from a medical fluid supply source;
a medical fluid outlet line through which the medical fluid is discharged toward an administration target;
a first branch line and a second branch line branching off from the medical fluid inlet line, the first branch line and the second branch line being connected to the medical fluid outlet line;
a medical fluid pumping bag provided on the first branch line, the medical fluid pumping bag storing therein medical fluid flowing along the first branch line, and being compressed by external force applied thereto to send the stored medical fluid under pressure to the medical fluid outlet line; and
temporary storage and supply means for temporarily storing the medical fluid sent under pressure from the medical fluid pumping bag and continuously discharging the temporarily stored medical fluid through the medical fluid outlet line, wherein the temporary storage and supply means comprises:
a temporary storage balloon provided on the medical fluid outlet line, wherein the temporary storage balloon inflates as medical fluid sent under pressure from the first branch line is drawn into the temporary storage balloon, and the temporary storage balloon discharges continuously the temporarily stored medical fluid using contractile force by which the temporary storage balloon is returned to an original state thereof, when the external force applied to the medical fluid pumping bag is released.

2. The medical fluid dispenser as set forth in claim 1, wherein the temporary storage and supply means further comprises: a medical fluid outlet tube forming a portion of the medical fluid outlet line so that medical fluid is sent under pressure from the first branch line into medical fluid outlet tube, with at least one hole formed in a circumferential surface of the medical fluid outlet tube, and
the temporary storage balloon is fitted over the circumferential surface of the medical fluid outlet tube in such a way that the temporary storage balloon covers the hole so that the temporary storage balloon is inflated by medical fluid flowing out from the medical fluid outlet tube through the hole to temporarily store the medical fluid therein and is returned to the original state thereof to supply the temporarily stored medical fluid into the medical fluid outlet tube through the hole.

3. The medical fluid dispenser as set forth in claim 2, wherein the temporary storage and supply means further comprises:
a backflow prevention device preventing the temporarily stored medical fluid from flowing backwards from the temporary storage balloon toward the first branch line,
the backflow prevention device comprising a check valve provided on an inlet side of the medical fluid outlet tube.

4. The medical fluid dispenser as set forth in claim 2, wherein the medical fluid outlet tube has a partition partitioning an inner space of the medical fluid outlet tube into an inlet side space, into which medical fluid is sent under pressure from the medical fluid pumping bag, and an outlet side space from which the medical fluid is discharged, and
the hole comprises an outflow hole communicating with the inlet side space, and an inflow hole communicating with the outlet side space.

5. The medical fluid dispenser as set forth in claim 4, wherein the temporary storage and supply means comprises:
a backflow prevention device preventing the temporarily stored medical fluid from flowing backwards from the temporary storage balloon toward the first branch line,
the backflow prevention device comprising an open and close member coming into close contact with the circumferential surface of the medical fluid outlet tube to close the outflow hole, the open and close member being moved away from the outflow hole by medical fluid sent under pressure to flow out of the outflow hole, thus opening the outflow hole.

6. The medical fluid dispenser as set forth in claim 5, wherein the open and close member has a tubular shape and is fitted over the medical fluid outlet tube, the open and close member being made of elastic material so that the open and close member is elastically brought into close contact with the outflow hole and is elastically changed in shape and moved away from the outflow hole by the medical fluid sent under pressure to flow out of the outflow hole.

7. The medical fluid dispenser as set forth in claim 6, wherein a depression for receiving the open and close member is formed in a portion of the circumferential surface of the medical fluid outlet tube over which the open and close member is fitted.

8. A medical fluid dispenser, comprising:

- a medical fluid inlet line into which medical fluid is supplied from a medical fluid supply source;
- a medical fluid outlet line through which the medical fluid is discharged toward an administration target;
- a first branch line and a second branch line branching off from the medical fluid inlet line, the first branch line and the second branch line being connected to the medical fluid outlet line;
- a medical fluid pumping bag provided on the first branch line, the medical fluid pumping bag storing therein medical fluid flowing along the first branch line, and being compressed by external force applied thereto to send the stored medical fluid under pressure to the medical fluid outlet line;
- a casing containing the medical fluid pumping bag therein;
- a compression button provided on the casing to enable the medical fluid pumping bag to be pressed by the compression button so that when the compression button is pressed, the external force is applied to the medical fluid pumping bag; and
- temporary storage and supply means for temporarily storing the medical fluid sent under pressure from the medical fluid pumping bag and continuously discharging the temporarily stored medical fluid through the medical fluid outlet line, wherein at least a portion of the first branch line through which medical fluid sent from the medical fluid pumping bag flows is made of a compressible soft tube, wherein the temporary storage and supply means comprises:

- a temporary storage balloon provided on the medical fluid outlet line, wherein the temporary storage balloon inflates as medical fluid sent under pressure from the first branch line is drawn into the temporary storage balloon, and the temporary storage balloon discharges the medical fluid using contractile force by which the temporary storage balloon is returned to an original state thereof; and
- a backflow prevention device preventing the temporarily stored medical fluid from flowing backwards from the temporary storage balloon toward the first branch line, wherein the backflow prevention device comprises a passage opening control unit opening or closing a passage of the first branch line in such a way that when no external force is applied to the medical fluid pumping bag, the medical fluid stored in the medical fluid pumping bag is interrupted from flowing into the medical fluid outlet line and when the external force is applied to the medical fluid pumping bag by pressing the compression button, the passage of the first branch line opens to allow the medical fluid sent under pressure from the medical fluid pumping bag to flow into the medical fluid outlet line, and wherein the passage opening control unit comprises:

- a pressing member mounted to the casing so as to be movable away from or approachable the soft tube so that when the pressing member approaches the soft tube, the pressing member compresses the soft tube to close a passage of the soft tube;
- a torsion spring providing elastic force to the pressing member so that the soft tube is compressed by the pressing member; and
- interlocking means for transmitting operating force, generated when the compression button is pressed, to the pressing member so that the pressing member is moved away from the soft tube.

9. The medical fluid dispenser as set forth in claim 8, wherein the pressing member comprises a pressing lever having a pressing part moving away from or approaching the soft tube depending on a direction in which the pressing lever rotates, and the passage opening control unit further comprises a stopper disposed in a radius of rotation of the pressing part, with the soft tube located between the stopper and the pressing lever, so that the stopper assists the pressing part in compressing the soft tube.

10. The medical fluid dispenser as set forth in claim 9, wherein the pressing lever rotates around an axis parallel to a direction in which the compression button is pressed, and the interlocking means comprises: a driven part provided on the pressing lever; and a drive part provided on the compression button at a position at which the drive part is able to come into contact with the driven part, wherein at least one of contact surfaces between the drive part and the driven part comprises a ramp so that when the compression button is pressed, the pressing lever rotates in a direction in which the pressing part that has compressed the soft tube releases the soft tube.

* * * * *

UNITED STATES PATENT AND TRADEMARK OFFICE
CERTIFICATE OF CORRECTION

PATENT NO. : 8,512,284 B2  Page 1 of 1
APPLICATION NO. : 13/146302
DATED : August 20, 2013
INVENTOR(S) : Young Gyu Lee It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this

Fifteenth Day of September, 2015

Michelle K. Lee
*Director of the United States Patent and Trademark Office*